(12) United States Patent  (10) Patent No.: US 7,628,770 B2
Ethelfeld  (45) Date of Patent: Dec. 8, 2009

(54) PIVOTABLE NEEDLE UNIT

(75) Inventor: Erik Winkel Ethelfeld, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 361 days.

(21) Appl. No.: 11/266,821

(22) Filed: Nov. 4, 2005

(65) Prior Publication Data
US 2006/0135913 A1 Jun. 22, 2006

Related U.S. Application Data

(63) Continuation of application No. PCT/DK2004/000332, filed on May 10, 2004.

(60) Provisional application No. 60/471,011, filed on May 16, 2003.

(30) Foreign Application Priority Data
May 8, 2003 (DK) ............... PA 2003 00696

(51) Int. Cl.
A61M 5/178 (2006.01)
A61M 25/00 (2006.01)

(52) U.S. Cl. .................. 604/164.08; 604/263
(58) Field of Classification Search ........ 604/110, 604/192–198, 288.01–288.04, 187, 82, 201, 604/191, 86, 523, 263, 164.08, 164.04, 164.12, 604/132, 136; D24/130
See application file for complete search history.

(56) References Cited

U.S. PATENT DOCUMENTS

| 55,711 | A | 6/1866 | Regester |
| 69,546 | A | 10/1867 | DeForest |
| 123,740 | A | 2/1872 | Stevens |
| 858,001 | A | 6/1907 | Howe |
| 2,605,765 | A | 8/1952 | Kollsman |
| 4,340,048 | A | 7/1982 | Eckenhoff |
| 4,552,561 | A | 11/1985 | Eckenhoff et al. |
| 5,527,288 | A | 6/1996 | Gross et al. |
| 5,584,808 | A | * | 12/1996 | Healy ............ 604/86 |
| 5,814,020 | A | 9/1998 | Gross |
| 5,851,197 | A | 12/1998 | Marano et al. |

(Continued)

FOREIGN PATENT DOCUMENTS

EP  937475  1/1999

(Continued)

Primary Examiner—Kevin C. Sirmons
Assistant Examiner—Elizabeth R Moulton
(74) Attorney, Agent, or Firm—Marc A. Began

(57) ABSTRACT

The present invention generally relates to the insertion of needles or needle-like members. Thus, a device comprises a housing having a mounting surface adapted for application to the skin of a subject, and a needle unit connected to the housing by a hinge allowing the needle unit to pivot corresponding to a pivoting axis defined by the hinge, the pivoting axis being arranged substantially in parallel with the mounting surface. The needle unit comprises a needle having a distal pointed portion adapted to penetrate the skin of the subject, the distal portion extending generally perpendicular to the mounting surface, and a proximal portion arranged substantially corresponding to the pivoting axis, whereby the needle unit is arranged to pivot between a first position in which the distal portion of the needle is retracted within the housing, and a second position in which the distal portion projects relative to the mounting surface. The needle may e.g. be in the form of a hollow needle or a needle sensor.

11 Claims, 13 Drawing Sheets

U.S. PATENT DOCUMENTS

| | | |
|---|---|---|
| 5,858,001 A | 1/1999 | Tsals et al. |
| 5,931,814 A | 8/1999 | Alex et al. |
| 5,957,895 A * | 9/1999 | Sage et al. .................. 604/181 |
| 6,280,148 B1 | 8/2001 | Zengerle et al. |
| 6,500,150 B1 | 12/2002 | Gross et al. |
| 2003/0069546 A1 * | 4/2003 | Sandstrom et al. .......... 604/263 |
| 2004/0115068 A1 * | 6/2004 | Hansen et al. .............. 417/379 |

FOREIGN PATENT DOCUMENTS

| | | |
|---|---|---|
| EP | 1177802 | 7/2001 |
| WO | 02/15965 | 2/2002 |
| WO | 2004/029457 | 4/2004 |

\* cited by examiner

Fig. 6A
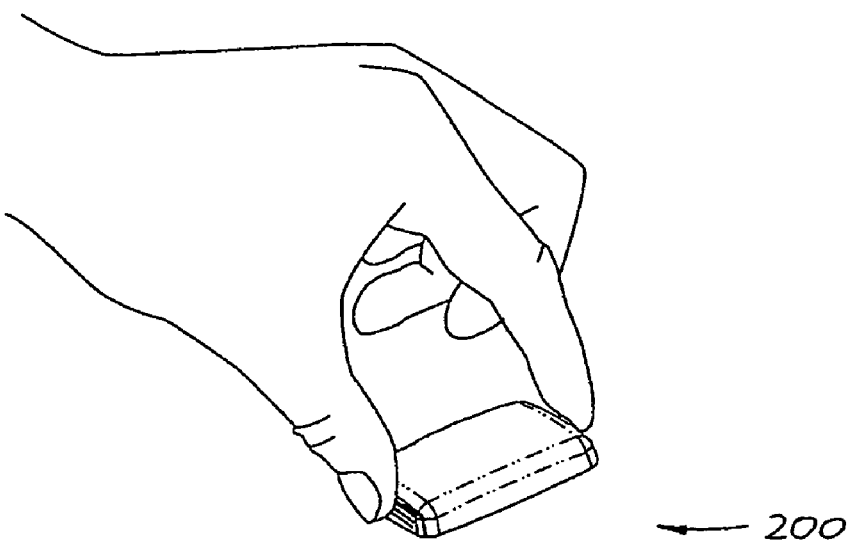
Fig. 6B
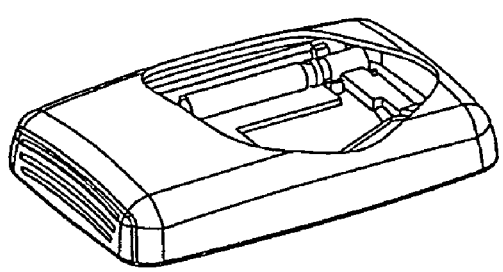
Fig. 6D
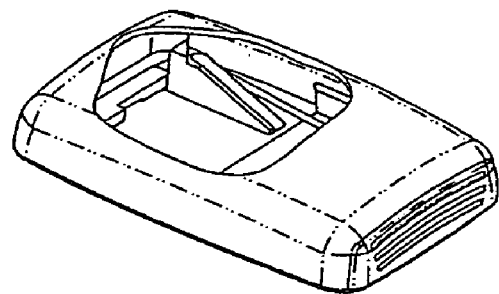
Fig. 6C
Fig. 6E
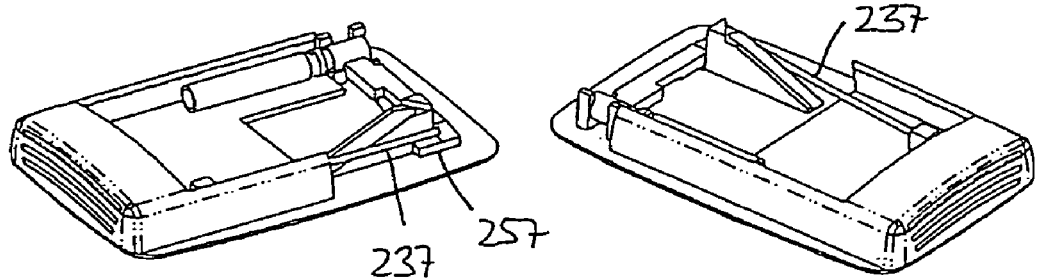

PIVOTABLE NEEDLE UNIT

CROSS REFERENCE TO RELATED APPLICATIONS

This application is a continuation of international application serial no. PCT/DK2004/000332 filed May 10, 2004 and claims priority of Danish application no. PA 2003 00696 filed May 8, 2003 and U.S. provisional application No. 60/471,011 filed May 16, 2003, all of which are hereby incorporated by reference.

The present invention generally relates to the insertion of transcutaneous devices such as needles, needle-like members and cannulas. More specifically, the invention relates to insertion of a transcutaneous device at a selected site within the body of a subject for subcutaneous, intravenous, intramuscular or intradermal delivery of a drug to the subject, the transcutaneous device being carried by a device comprising a mounting surface adapted for application to the skin of the subject. Especially, the invention relates to insertion of an infusion needle or cannula for the infusion of a drug, to insertion of a needle-formed sensor, as well as to insertion of insertion needles for easy placement of a device such as a sensor through the skin of a subject.

BACKGROUND OF THE INVENTION

In the disclosure of the present invention reference is mostly made to the treatment of diabetes by injection or infusion of insulin, however, this is only an exemplary use of the present invention.

Portable drug delivery devices for delivering a drug to a patient are well known and generally comprise a reservoir adapted to contain a liquid drug and having an outlet in fluid communication with a hollow infusion needle, as well as expelling means for expelling a drug out of the reservoir and through the skin of the subject via the hollow needle. Such devices are often termed infusion pumps.

Basically, infusion pumps can be divided into two classes. The first class comprises durable infusion pumps which are relatively expensive pumps intended for 3-4 years use, for which reason the initial cost for such a pump often is a barrier to this type of therapy. Although more complex than traditional syringes and pens, the pump offer the advantages of continuous infusion of insulin, precision in dosing and optionally programmable delivery profiles and user actuated bolus infusions in connections with meals.

Addressing the above problem, several attempts have been made to provide a second class of drug infusion devices that are low in cost and convenient to use. Some of these devices are intended to be partially or entirely disposable and may provide many of the advantages associated with an infusion pump without the attendant cost and inconveniencies, e.g. the pump may be prefilled thus avoiding the need for filling or refilling a drug reservoir. Examples of this type of infusion devices are known from U.S. Pat. Nos. 4,340,048 and 4,552, 561 (based on osmotic pumps), U.S. Pat. No. 5,858,001 (based on a piston pump), U.S. Pat. No. 6,280,148 (based on a membrane pump), U.S. Pat. No. 5,957,895 (based on a flow restrictor pump (also know as a bleeding hole pump)), U.S. Pat. No. 5,527,288 (based on a gas generating pump), or U.S. Pat. No. 5,814,020 (based on a swellable gel) which all in the last decades have been proposed for use in inexpensive, primarily disposable drug infusion devices, the cited documents being incorporated by reference.

The disposable pumps generally comprises a skin-contacting mounting surface adapted for application to the skin of a subject by adhesive means, and with the infusion needle arranged such that in a situation of use it projects from the mounting surface to thereby penetrate the skin of the subject, whereby the place where the needle penetrates the skin is covered while the appliance is in use.

The infusion needle may be arranged to permanently project from the mounting surface such that the needle is inserted simultaneously with the application of the infusion pump. Examples of this configuration can be found in U.S. Pat. Nos. 2,605,765, 4,340,048 and in EP 1 177 802. Although this configuration provides a simple and cost-effective solution, the actual user-performed piercing of the tissue with the needle is often problematic as people who are not experts in medicine are usually insufficiently practised to place such a needle correctly and they often suffer from a fear of the likely pain. Although not relating specifically to infusion pumps, U.S. Pat. No. 5,851,197 discloses an injector in which an infusion set comprising a skin-mountable surface with a protruding needle can be mounted, the injector upon actuation driving the entire infusion set into contact with a skin portion whereby the needle is inserted through the skin.

Addressing the above problem, infusion pump devices have been proposed in which the pump device is supplied to the user with the needle in a retracted state, i.e. with the distal pointed end of the needle "hidden" inside the pump device, this allowing the user to place the pump device on the skin without the possibility of observing the needle. When first the needle is hidden, at least some of the fear is overcome making the introduction of the needle in a second step less problematic. U.S. Pat. Nos. 5,858,001 and 5,814,020 disclose infusion devices of this type in which an infusion needle is arranged in an upper housing portion pivotably arranged relative to a base plate portion. In this way the user can introduce the needle by pressing the upper portion into engagement with the base plate portion.

To further reduce the fear and pain associated with the introduction of the needle, many recent pump devices have been provided with actuatable needle insertion means, which just has to be released by the user after which e.g. spring means quickly will advance the needle through the skin.

For example, U.S. Pat. No. 5,957,895 discloses a liquid drug delivery device comprising a bent injection needle which is adapted to project through a needle aperture in the bottom surface of the housing in a situation of use. A movable needle carrier is disposed in the housing for carrying the injection needle and for causing the injection end of the needle to project through the needle aperture upon movement of the needle carrier.

U.S. Pat. No. 5,931,814 discloses an infusion device having a housing with a drug reservoir, an infusion needle (or cannula) communicating with the reservoir, means for inserting the needle, and pump means for discharging the reservoir contents through the needle. The needle is fixed relative to the housing and projects beyond the lower skin-contacting surface of the housing to the depth required for injection. The needle is surrounded by a protective element which is moved by spring means from a first end position in which the protective device projects beyond the lower surface of the housing and beyond the needle to a second end position in which the protective device does not project beyond the underside of the casing. WO 02/15965 discloses a similar infusion device in which a base plate member acts as a protecting element until an upper part of the device, to which the needle is fixed, is moved down into engagement with the base plate member.

In the devices disclosed in U.S. Pat. Nos. 5,957,895 and 5,931,814 the needle is automatically inserted by the release of pre-tensioned spring means arranged within the devices, whereas in the device known from WO 02/15965 the needle is inserted by the user actively moving the hidden needle. Although the automatic needle insertion means adds convenience for the user and may serve to overcome needle fear, such means also adds to the complexity and thus to the cost of the device, they may reduce the reliability, just as they may add to the bulkiness of the device.

In the above primarily infusion devices has been discussed, however, the problem of inserting a needle-formed device through the skin of a subject also relates to other fields, e.g. the introduction of needle-formed sensors comprising sensor means capable of being influenced by a body substance and producing a signal corresponding thereto (e.g. blood glucose).

DISCLOSURE OF THE INVENTION

Having regard to the above-identified problems, it is an object of the present invention to provide an insertion means for a transcutaneous device mounted in a device and which allows for easy and swift insertion of the transcutaneous device, yet is reliable in use. The device should be compact in size and be designed for cost effective manufacturing.

Correspondingly, a medical device is provided, comprising a housing having a mounting surface adapted for application to the skin of a subject, and a transcutaneous device unit connected to the housing thereby providing a hinge allowing the transcutaneous device unit or a portion thereof to pivot corresponding to a pivoting axis defined by the hinge, the pivoting axis being arranged substantially in parallel with the mounting surface. The transcutaneous device unit comprises a transcutaneous device having a distal pointed portion adapted to penetrate the skin of the subject, the distal portion extending generally perpendicular to the mounting surface, and a proximal portion arranged substantially corresponding to the pivoting axis, whereby the transcutaneous device unit is arranged to pivot between a first position in which the distal portion of the transcutaneous device is retracted within the housing, and a second position in which the distal portion projects relative to the mounting surface.

Correspondingly, a medical device is provided, comprising a housing having a mounting surface adapted for application to the skin of a subject, and a transcutaneous device unit connected to the housing thereby providing a hinge allowing the needle unit or a portion thereof to pivot corresponding to a pivoting axis defined by the hinge, the pivoting axis being arranged substantially in parallel with the mounting surface. The transcutaneous device unit comprises a transcutaneous device, the transcutaneous device comprising a distal pointed portion adapted to penetrate the skin of the subject, the distal portion extending generally perpendicular to the mounting surface, and a proximal portion arranged substantially corresponding to the pivoting axis, whereby the transcutaneous device unit is arranged to provide a pivoting movement between a first position in which the distal portion of the needle is retracted within the housing, and a second position in which the inlet portion projects relative to the mounting surface. The hinge may be formed by the unit or between the unit and the housing. In this way the invention provides a transcutaneous device unit which can be actuated and connected without relying on sliding (e.g. linear) movement of the transcutaneous device unit and without having to bent the transcutaneous device.

The transcutaneous device may e.g. be in the form of a pointed hollow infusion needle, a pointed needle sensor, or a combination of a relatively flexible per se blunt cannula or sensor device with a pointed insertion needle may provide a pointed transcutaneous device, the insertion needle being retractable after insertion of the blunt portion of the transcutaneous device. The cannula is advantageously soft and flexible relative to the insertion needle which typically is a solid steel needle. However, the transcutaneous device may also be a composite structure comprising a distal portion, a proximal portion and an intermediate portion provided by different types of conduits. For example, a transcutaneous device unit may comprise a distal portion in the form of a cannula in combination with an insertion needle, a proximal portion in the form of a hollow infusion-type needle, and an intermediate portion connecting the distal and proximal portions and being formed in a carrier member in which the distal and proximal portions are mounted. The distal portion may also be in the form of a micro needle array. In the disclosure of the present invention as well as in the description of the exemplary embodiments, reference will mostly be made to a transcutaneous device in the form of a hollow infusion needle.

By this arrangement a distal end of a transcutaneous device can be moved between a retracted state and an extended state, yet providing a proximal end allowing a high degree of flexibility and reliability for connection to a fluid reservoir. For example, a fluid reservoir may be (or may be brought) in fluid communication with proximal end of the transcutaneous device before the needle unit is pivoted, or the fluid reservoir may be brought in fluid communication with the proximal end of the transcutaneous device during or after the transcutaneous device unit is pivoting. The only requirement for allowing this arrangement would be that the fluid connection allows rotation of the proximal transcutaneous device end and is moved axially corresponding to the pivoting axis.

Correspondingly, in an exemplary embodiment a medical device is provided, further comprising a reservoir adapted to contain a liquid drug and comprising in a situation of use an outlet in fluid communication with the transcutaneous device, and expelling means for expelling a drug out of the reservoir and through the skin of the subject via the transcutaneous device.

The reservoir advantageously comprises outlet means adapted to cooperate with the proximal portion of the transcutaneous device (thus serving as an inlet portion), the outlet means being arranged substantially corresponding to the pivoting axis, thereby allowing the transcutaneous device unit to pivot substantially without non-rotational displacement of the inlet portion of the transcutaneous device relative to the outlet means. In such an arrangement the reservoir and the inlet portion may be arranged moveable relative to each other, corresponding substantially to the pivoting axis, between a disconnected position in which there is no fluid communication between the reservoir and the inlet portion, and a connected position in which fluid communication between the reservoir and the inlet portion is established. Advantageously, the inlet portion of the transcutaneous device comprises a pointed proximal end, and the outlet means of reservoir comprises a needle-penetratable septum, e.g. a self-sealing elastomeric septum.

The transcutaneous device unit may be inserted manually, or the medical device may comprise actuatable driving means disposed within the housing and adapted to pivot the transcutaneous device unit from the first position to the second position. The driving means may be actuated by actuation means moveable, relative to the housing, from a first position to a second position thereby actuating the driving means. In an exemplary embodiment the reservoir is connected to the actuation means, whereby movement of the actuation means between the first and the second position causes the reservoir to be arranged in fluid communication with the transcutaneous device.

In an advantageous embodiment, the device comprises common actuation means moveable, relative to the housing, from a first position to a second position thereby actuating the driving means, wherein the reservoir is connected to the actuation means such that movement of the actuation means between the first and the second position causes the reservoir to be arranged in fluid communication with the transcutaneous device, the inlet portion of the transcutaneous device being introduced through the needle-penetratable septum either before or after the transcutaneous device unit is pivoted from the first position to the second position.

The transcutaneous device unit may be in the form of a "naked" needle, however, in advantageous embodiments the transcutaneous device unit comprises a carrier for the transcutaneous device, the transcutaneous device being carried by (or formed integrally with) the carrier, the carrier being connected to the housing by the hinge. The hinge may be provided by cooperating members of the carrier respectively the housing, or the carrier and the housing may be formed integrally connected to each other by a film-hinge.

Normally the transcutaneous device carrier would serve only as a carrier, however, the carrier may be provided with a pump for pumping a liquid between the inlet and outlet portion of the transcutaneous device.

For any of the above-described embodiments, the mounting surface advantageously comprises adhesive means for adhering the first unit to the skin of the subject.

In a further aspect, the present invention provides a transcutaneous device unit comprising first and second portions connected by a hinge allowing the first portion to pivot corresponding to a pivoting axis defined by the hinge. The first portion comprises a transcutaneous device having a distal pointed portion adapted to penetrate the skin of a subject, the distal portion extending from the first portion, and a proximal portion arranged substantially corresponding to the pivoting axis, whereby the first portion can be pivoted between a first position and a second position relative to the second portion and corresponding to the pivoting axis.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form. In the description of the exemplary embodiments reference will be made to the use of insulin. Correspondingly, the term "subcutaneous" infusion is meant to encompass any method of transcutaneous delivery to a subject. Further, the term needle (when not otherwise specified) defines a piercing member adapted to penetrate the skin of a subject.

BRIEF DESCRIPTION OF THE DRAWINGS

In the following the invention will be further described with references to the drawings, wherein FIGS. 6A-6E shows a second state of use corresponding to FIGS. 4A-4E.

In the figures like structures are identified by like reference numerals.

DESCRIPTION OF EXEMPLARY EMBODIMENTS

When in the following terms as "upper" and "lower", "right" and "left", "horizontal" and "vertical" or similar relative expressions are used, these only refer to the appended figures and not to an actual situation of use.

FIGS. 1-3 show in schematic representations perspective views of different states of use of a medical device in accordance with the invention. Correspondingly, the configuration of the different structures as well as there relative dimensions are intended to serve illustrative purposes only.

Figure 1A:
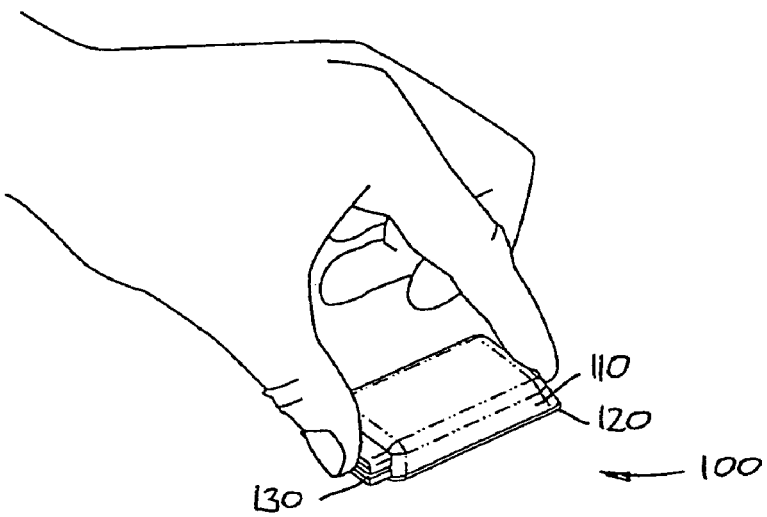
FIG. 1A shows in a perspective view a first embodiment of a medical device gripped by a user corresponding to a first state of use.
Figure 1B:
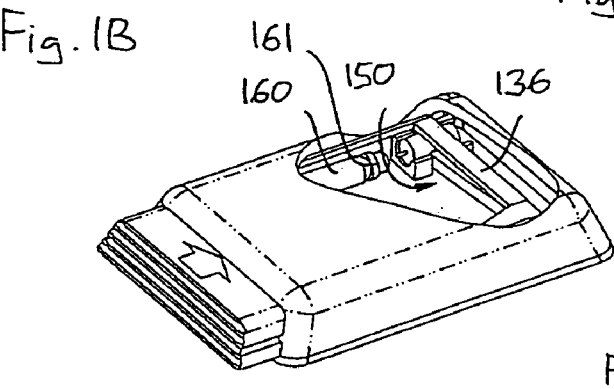
FIG. 1B shows the device of FIG. 1A with a portion of the housing cut off.
Figure 1D:
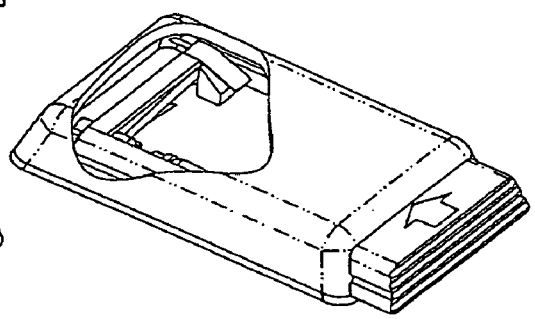
FIG. 1D shows the device of FIG. 1A seen from a different angle with a portion of the housing cut off.
Figure 1C:
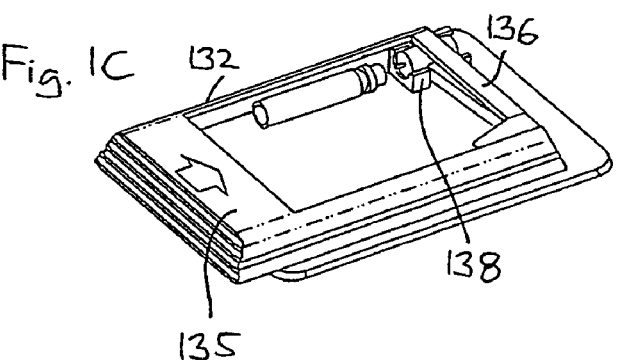
FIG. 1C shows the device of FIG. 1A with a portion of the housing removed.
Figure 1E:
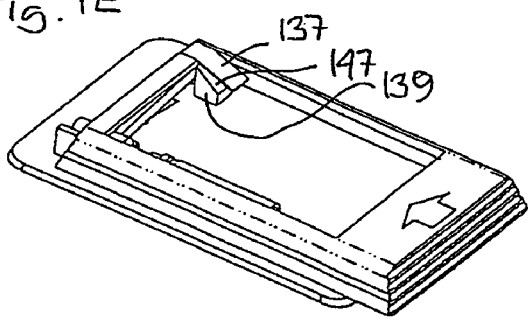
FIG. 1E shows the device of FIG. 1D with a portion of the housing removed.
Figure 2A:
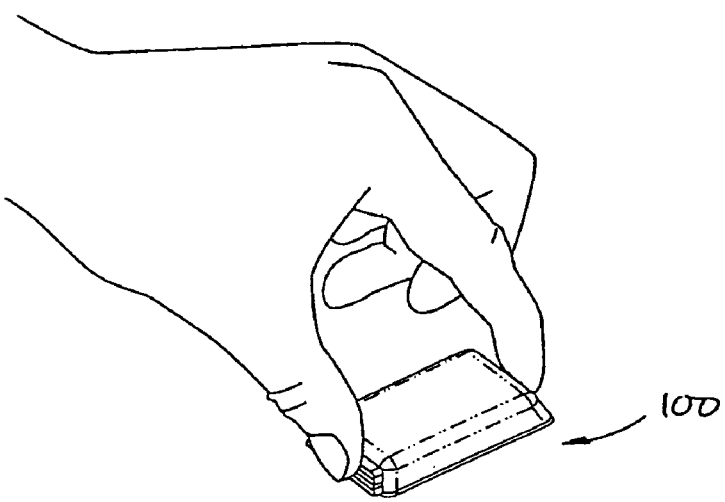
FIGS. 2A-2E shows an intermediate state of use corresponding to FIGS. 1A-1E.
Figure 2B:
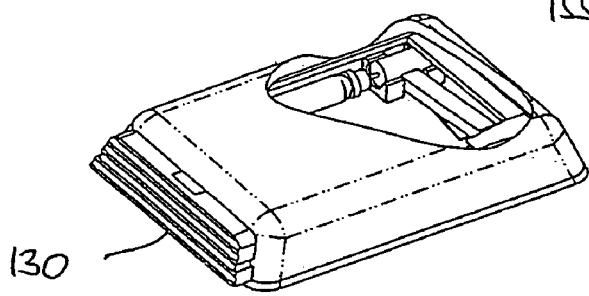
Figure 2D:
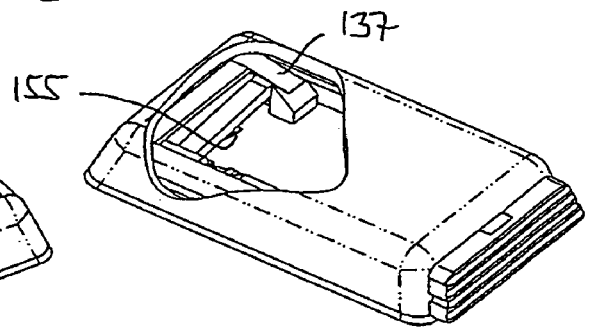
Figure 2C:
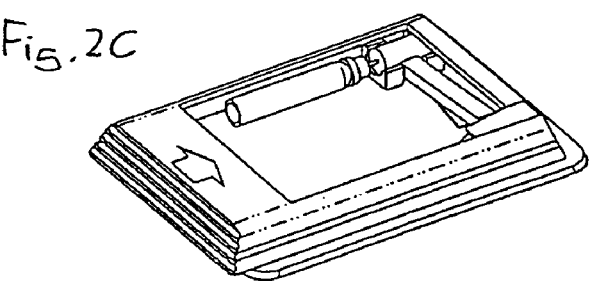
Figure 2E:
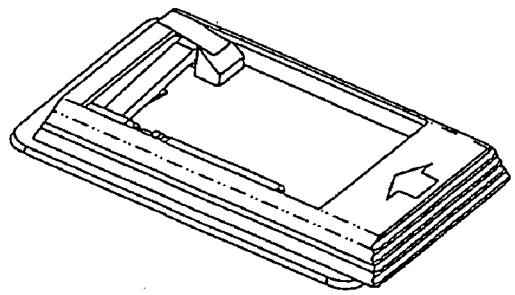
Figure 3A:
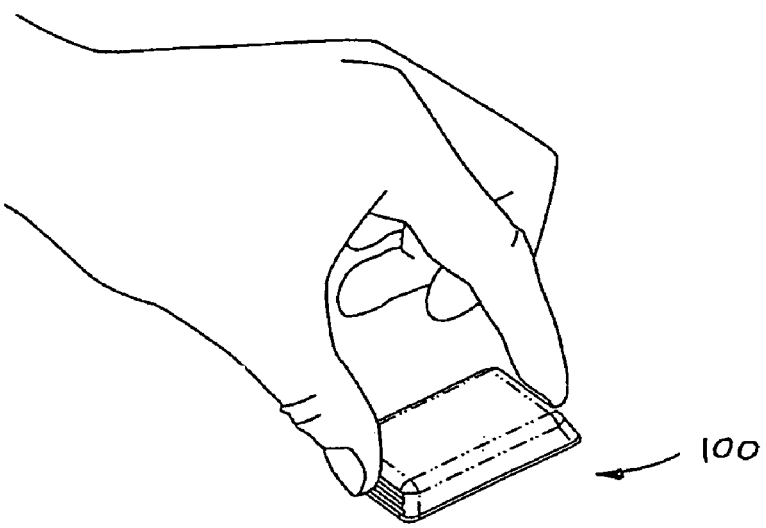
FIGS. 3A-3E shows a second state of use corresponding to FIGS. 1A-1E.
Figure 3B:
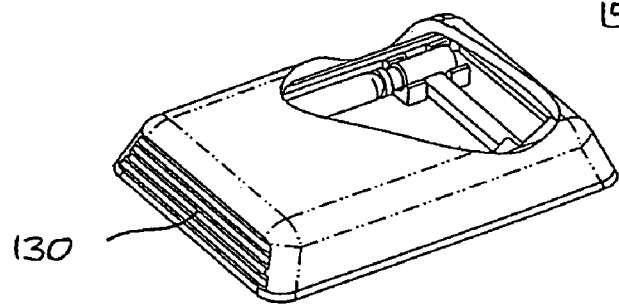
Figure 3D:
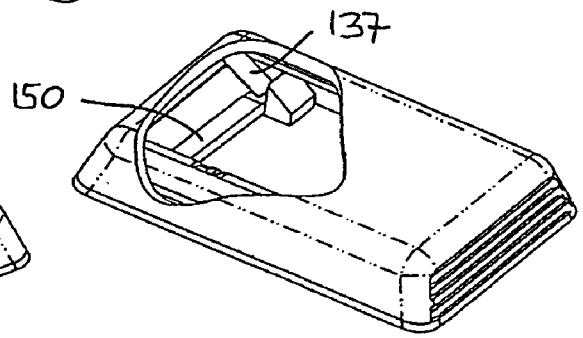
Figure 3C:
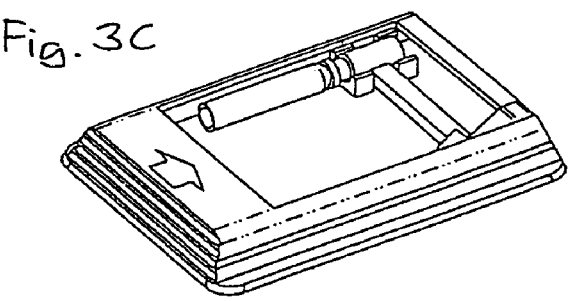
Figure 3E:
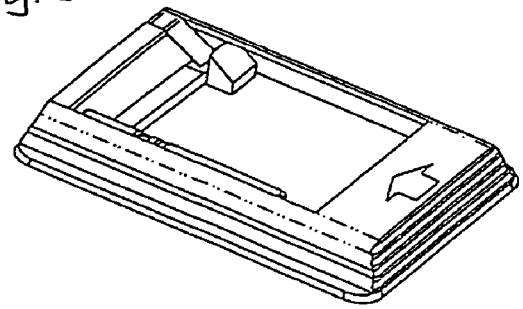
Figure 4A:
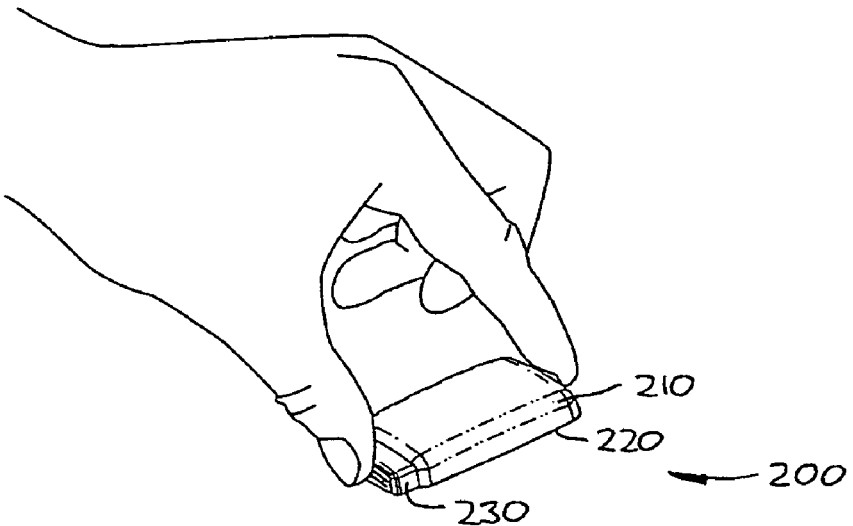
FIG. 4A shows in a perspective view a second embodiment of a medical device gripped by a user corresponding to a first state of use.
Figure 4B:
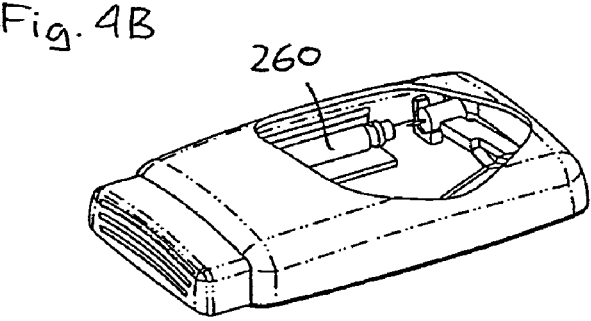
FIG. 4B shows the device of FIG. 4A with a portion of the housing cut off.
Figure 4D:
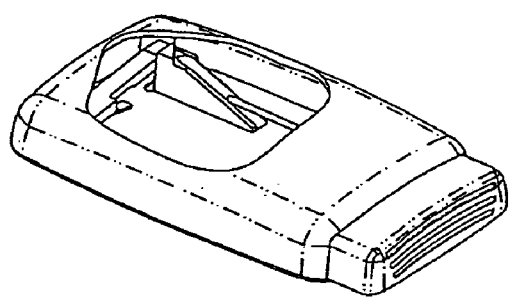
FIG. 4D shows the device of FIG. 4A seen from a different angle with a portion of the housing cut off.
Figure 4C:
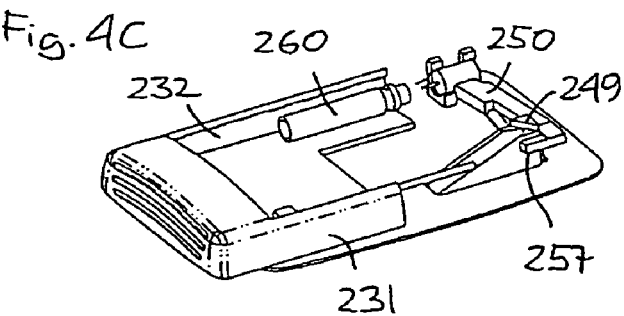
FIG. 4C shows the device of FIG. 4A with a portion of the housing removed.
Figure 4E:
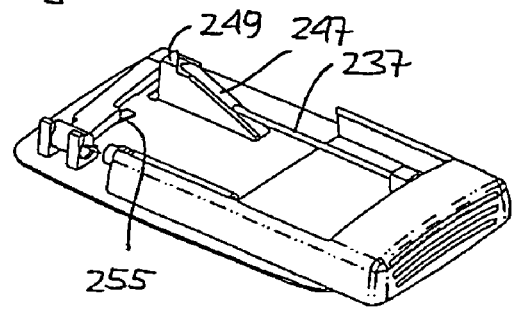
FIG. 4E shows the device of FIG. 4D with a portion of the housing removed.
Figure 5A:
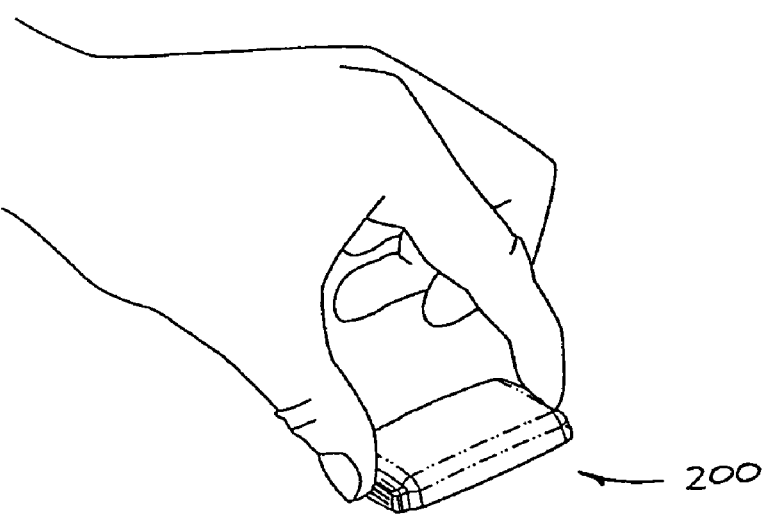
FIGS. 5A-5E shows an intermediate state of use corresponding to FIGS. 4A-4E.
Figure 5B:
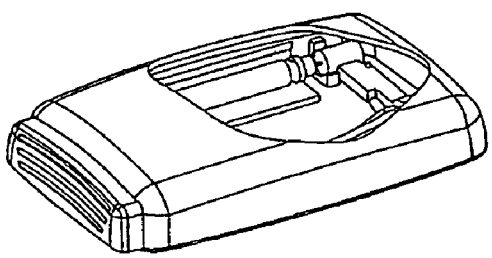
Figure 5D:
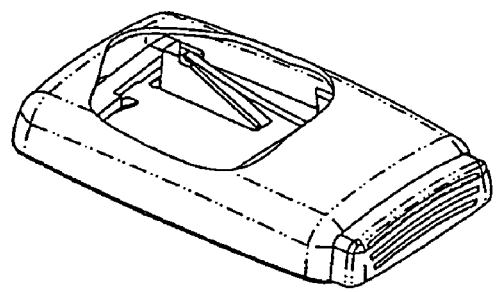
Figure 5C:
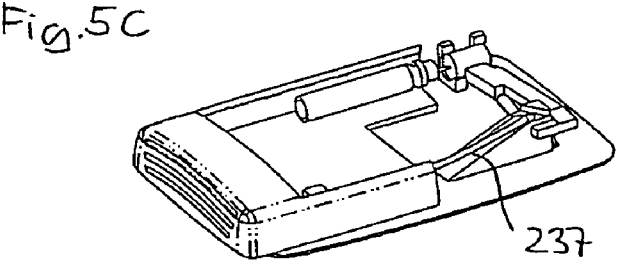
Figure 5E:
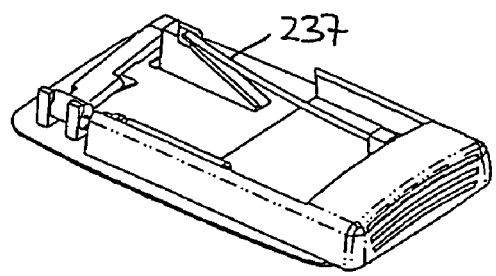

More specifically, FIG. 1A shows a first embodiment of a medical device 100 gripped by a user. The medical device comprises a housing with an upper housing portion 110 and a lower base plate portion 120, the housing providing a cavity in which an actuation member 130 is slidingly received through an opening, the actuation element being moveable corresponding to a longitudinal direction in respect of the device. The base plate portion comprises an adhesive mounting surface 121 adapted for application to the skin of a subject, the mounting surface being generally planar and defining a general plane. The actuation member comprises a ribbed area allowing for easy gripping by a user, e.g. using the first and second fingers as shown.

In the shown embodiment the actuation member is formed as a frame having opposed side portions 131, 132 adapted to be in sliding engagement with inner surface portions of the upper housing portions, the inner surface portions comprising longitudinally ridges received in corresponding grooves formed on the outer surfaces of the side portions. The two side portions are connected by a button portion 135 corresponding to an outer end and by a bridge portion 134 corresponding to an inner end thereof, the bridge portion comprising a spring means in the form of a leaf spring 137 having a free end portion with an inclined orientation relative to the base plate portion, the leaf spring serving as an insertion spring. The leaf spring may be attached to the bridge portion (e.g. when made from a metal alloy) or it may be formed integrally with the actuation member (e.g. manufactured from a polymer). The base plate portion comprises an upper surface on which a female hinge member 138 and a ramp member 139 are formed, preferably formed integrally with the base plate portion. The ramp member comprises an upper inclined ramp surface 147 adapted to engage a lower surface of the leaf spring 137 (serving as a drive portion adapted to engage a corresponding engagement portion on the needle unit), the ramp surface terminating in an upper free edge 148.

The device further comprises a needle unit 150 connected to the base plate portion by a hinge allowing the needle unit to pivot corresponding to a pivoting axis defined by the hinge, the pivoting axis being arranged substantially in parallel with the mounting surface. The needle unit comprises a hollow infusion needle (see FIG. 7A) having a distal pointed outlet portion 151 adapted to penetrate the skin of the subject, the outlet portion extending generally perpendicular to the mounting surface, and a pointed proximal inlet portion 152 arranged substantially corresponding to the pivoting axis. The distal end may be straight or curved, e.g. arcuate corresponding to the pivoting axis. The needle is carried by a needle carrier comprising an arm portion 153 and a cylindrical male hinge portion, the needle carrier being connected to the female hinge member thereby forming the hinge. The arm comprises a biasing member in the form of a leaf spring 155 projecting therefrom, the spring being in engagement with the upper surface of the base plate member thereby providing an upwardly directed biasing force forcing the needle into its initial position.

By this arrangement the needle unit can pivot between an initial position in which the inlet portion of the needle is retracted within the housing, and a second position in which the inlet portion projects relative to the mounting surface through an opening (not to be seen in the figs.) formed in the base plate portion. In the disclosed embodiments the hinge is provided by cooperating members of the needle carrier respectively the housing, however, a "naked" needle may be connected to the housing or the needle carrier and the housing may be formed integrally connected to each other by a film-hinge.

The device further comprises a reservoir 160 adapted to contain a liquid drug and comprising in a situation of use an outlet in fluid communication with the infusion needle, and expelling means (not shown for better illustrating the principles of the invention) for expelling a drug out of the reservoir and through the skin of the subject via the hollow needle. The reservoir and the expelling means are mounted on the actuation member and thus moveable relative to the housing. The reservoir comprises a needle-penetratable septum 161 adapted to cooperate with the inlet portion of the infusion needle, the septum being arranged substantially corresponding to the pivoting axis, thereby allowing the needle unit to pivot substantially without non-rotational displacement of the inlet portion of the infusion needle relative to the septum.

With reference to FIGS. 2 and 3 use and actuation of the device 100 will be described.

After having placed the medical device on a skin portion, the user presses the actuation member 130 into the housing whereby the needle is inserted and the delivery means started. During this action the actuation member is moved from a first (initial) position through an intermediate position to a second position. During movement of the actuation member from the first to the intermediate position the insertion spring 137 is moved relative to the ramp member, this causing an upwards activation movement of the drive portion whereby energy is releasably stored in the spring, and a displacement movement in which the drive portion is moved to a position above the engagement portion of the needle unit. At the same time the reservoir is moved into fluid communication with the infusion needle. After this, actuation of the actuation member from the intermediate to the second position causes release of the activated spring (when the distal free edge of the insertion spring slides over the upper free edge of the ramp, whereby the insertion spring in a snap-action engages the needle unit thereby biasing it downwardly to its second position against the force of the biasing spring 155. At the same time the actuation member is locked in place by the insertion spring being locked behind the ramp member.

The delivery means or sensor electronics will have to be actuated in combination with insertion of the needle, either in combination with the above-described actuation of the needle (e.g. by closing an electric contact or by providing a fluid communication) or by using additional actuation means which may be operated separately after the device has been mounted on the skin and the needle introduced.

In FIGS. 4-6 is shown a second embodiment of a medical device 200 similar to the first embodiment, the device comprising an upper housing portion 210 and a lower base plate portion 220, the housing providing a cavity in which an actuation member 230 is slidingly received through an opening, the actuation element being moveable corresponding to a longitudinal direction. The device further comprises a reservoir 260 and a needle unit 250. The device also comprises an inserter spring 237 and a ramp member 247, however, in contrast to the first embodiment the inserter spring is in the form of a thin rod just as the ramp member is arranged to deflect the inserter spring upwards as well as sidewards.

More specifically, the ramp surface is somewhat longer and has a concave cross-sectional configuration, this allowing the rod spring to slide thereon without accidental disengagement. The ramp terminates in an obliquely oriented deflection wall 249 which will force the spring rod outwards when forced thereagainst. The rod may be formed integrally with the actuation member or attached as a separate member, e.g. as a metal string. The needle unit is similar to the first embodiment apart from comprising a separately formed engagement portion 257 projecting from the distal end of the carrier arm and arranged on the side of the ramp member just below the deflection wall. Further, in contrast to the first embodiment, the actuation member does not comprise a bridge portion connecting the inner ends of the side portions.

In use, the second embodiment is actuated in the same way as the first embodiment, the primary difference being that the insertion spring is released from the upper ramp surface by a sidewards movement provided by the deflection wall.

In the above described embodiments, the actuation member has been moved linearly, however, it may other movements may be utilized in accordance with the invention. For example, a medical device may have a circular configuration in which actuation may be provided by the user rotating an upper portion of the housing. In such an arrangement the insertion spring may extend radially with a free peripheral end sliding on a curved ramp.

Figure 7A:
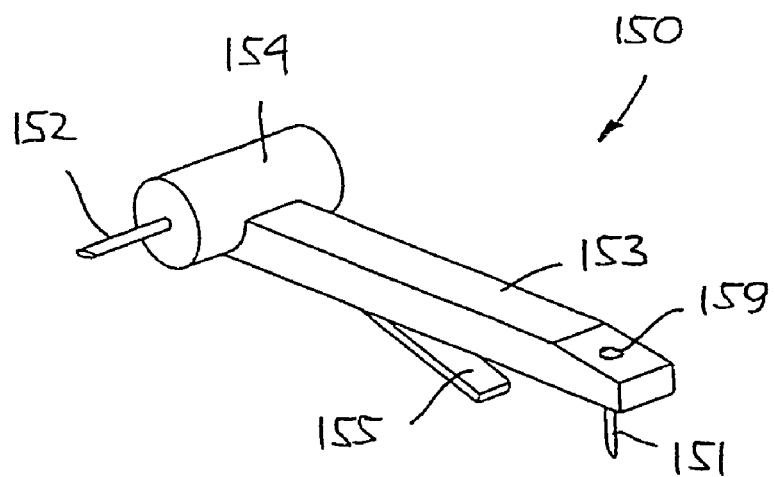
FIG. 7A shows a transcutaneous device unit.
Figure 9A:
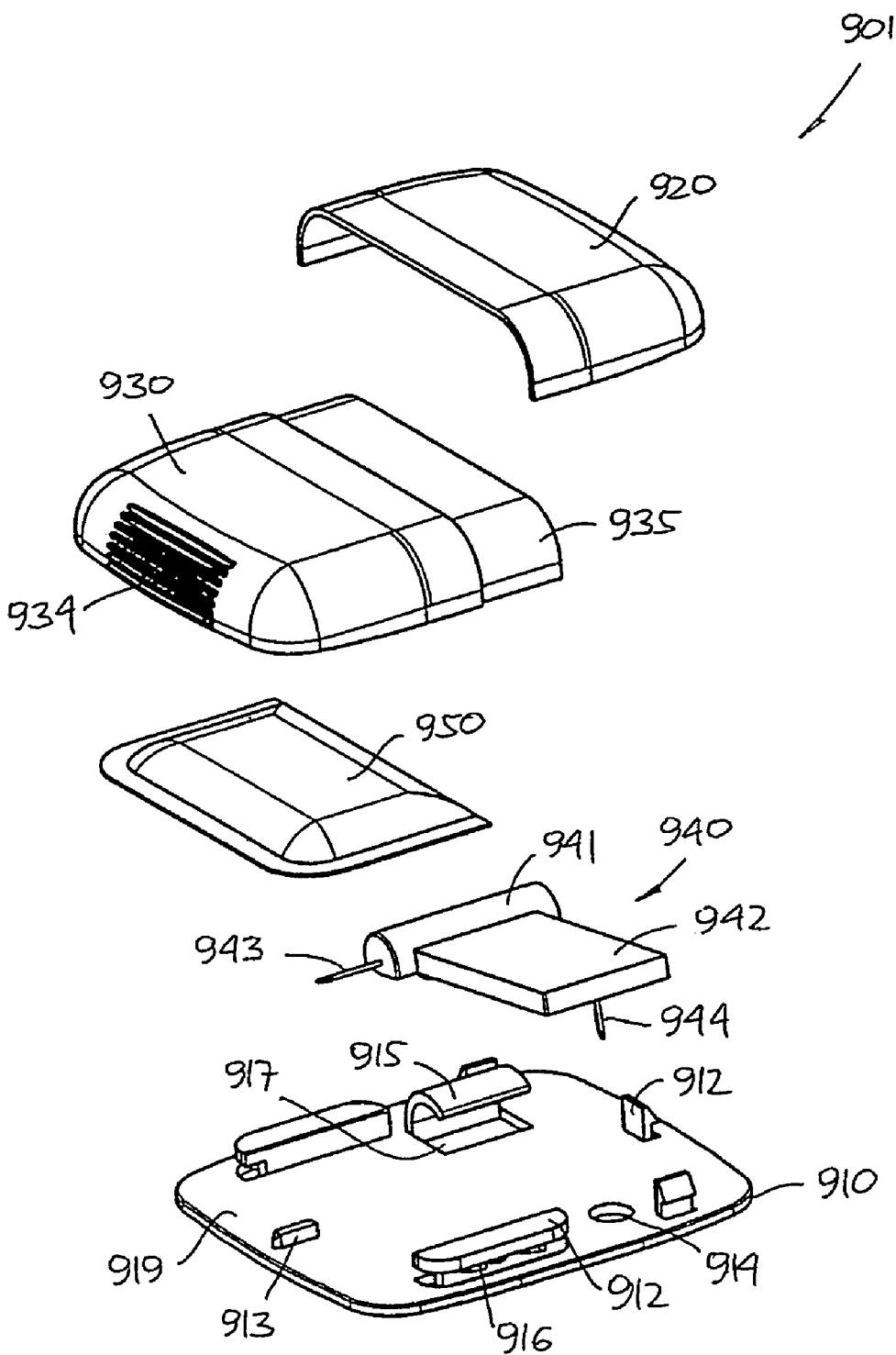
FIG. 9A shows an exploded view of a drug infusion device seen from above.
Figure 9B:
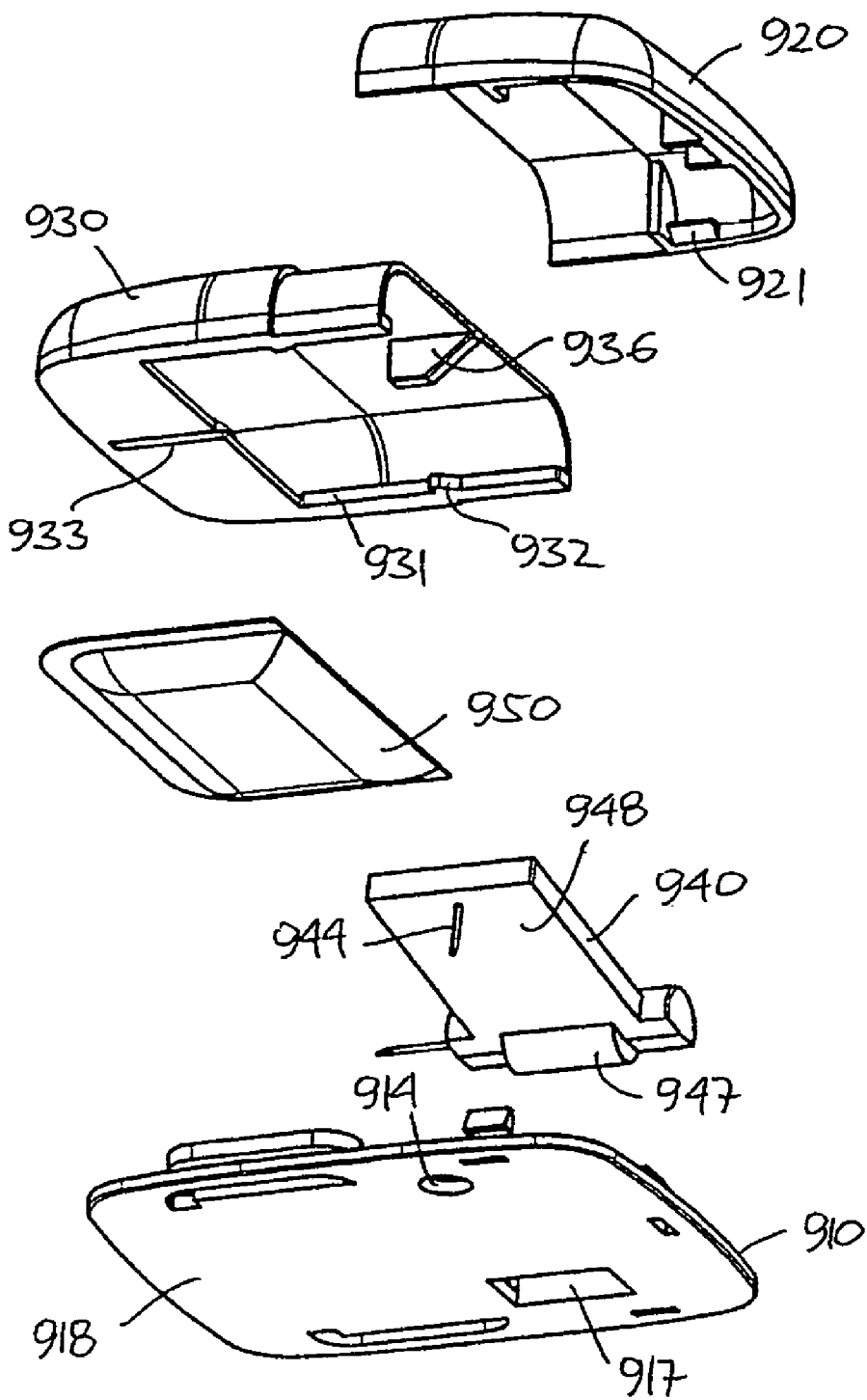
FIG. 9B shows an exploded view of the infusion device seen of FIG. 9A from below.
Figure 9C:
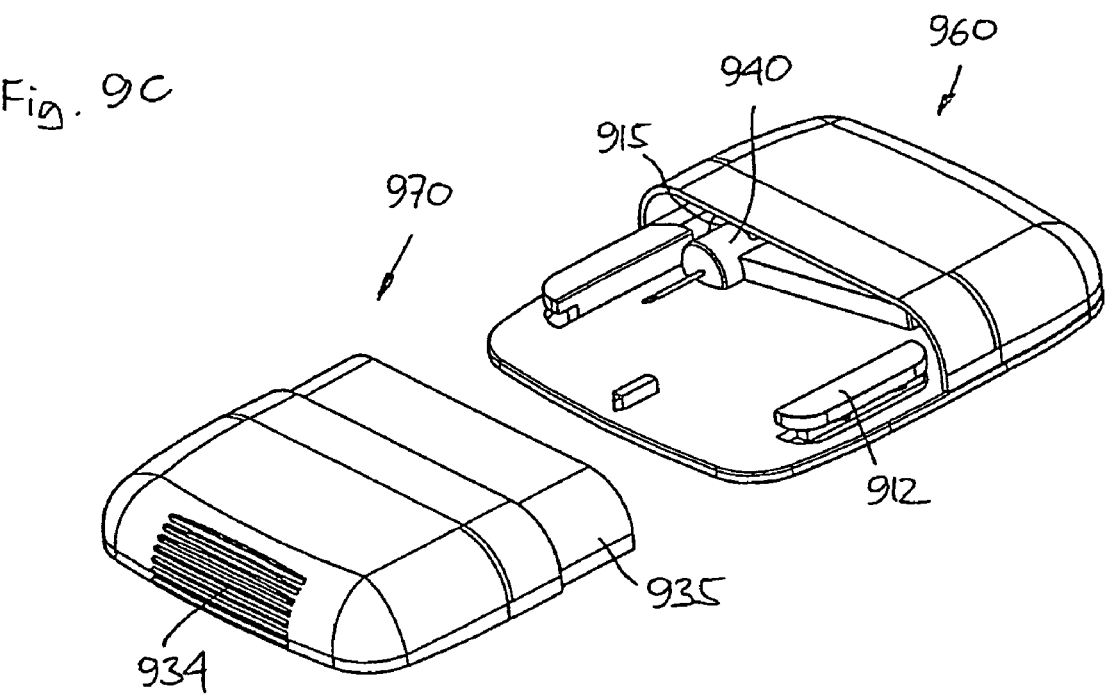
FIGS. 9C and 9D shows the infusion device comprising two sub-assemblies.
Figure 9D:
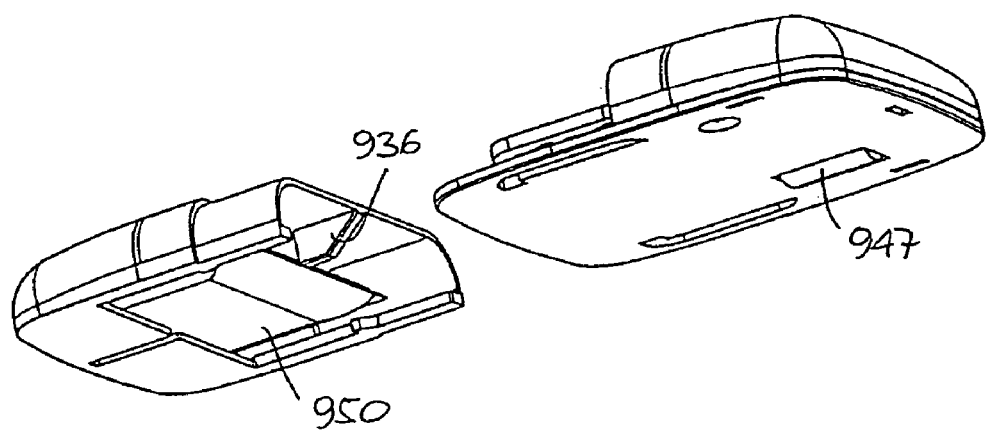

FIG. 7A shows a needle unit 150 adapted to be connected to a housing member by a hinge allowing the needle unit to pivot corresponding to a pivoting axis defined by the hinge. More specifically, the needle unit comprises a needle carrier having a cylindrical hinge portion 154 defining the pivoting axis, and an arm member 153 extending perpendicularly from the hinge portion in respect of the pivoting axis. On a lower surface of the arm member a biasing means is arranged in the form of a leaf spring member 155 adapted to engage a portion of the housing. The needle carrier carries a needle having a distal pointed portion 151 adapted to penetrate the skin of the subject, the distal portion extending generally perpendicular to the mounting surface, and a proximal portion (152) arranged substantially corresponding to the pivoting axis. In this way the needle unit can be arranged to pivot between a first position in which the distal portion of the needle is retracted within a housing, and a second position in which the inlet portion projects relative to a mounting surface. In case the distal portion is in the form of cannula, the arm member may be provided with a needle-penetratable septum 159 allowing an insertion needle to be inserted through the cannula as shown in FIG. 9A. In the shown embodiment the carrier may be injection moulded around a needle, however, the carrier may also be formed from sheet metal to which a needle is attached e.g. by adhesive or welding.

Figure 7B:
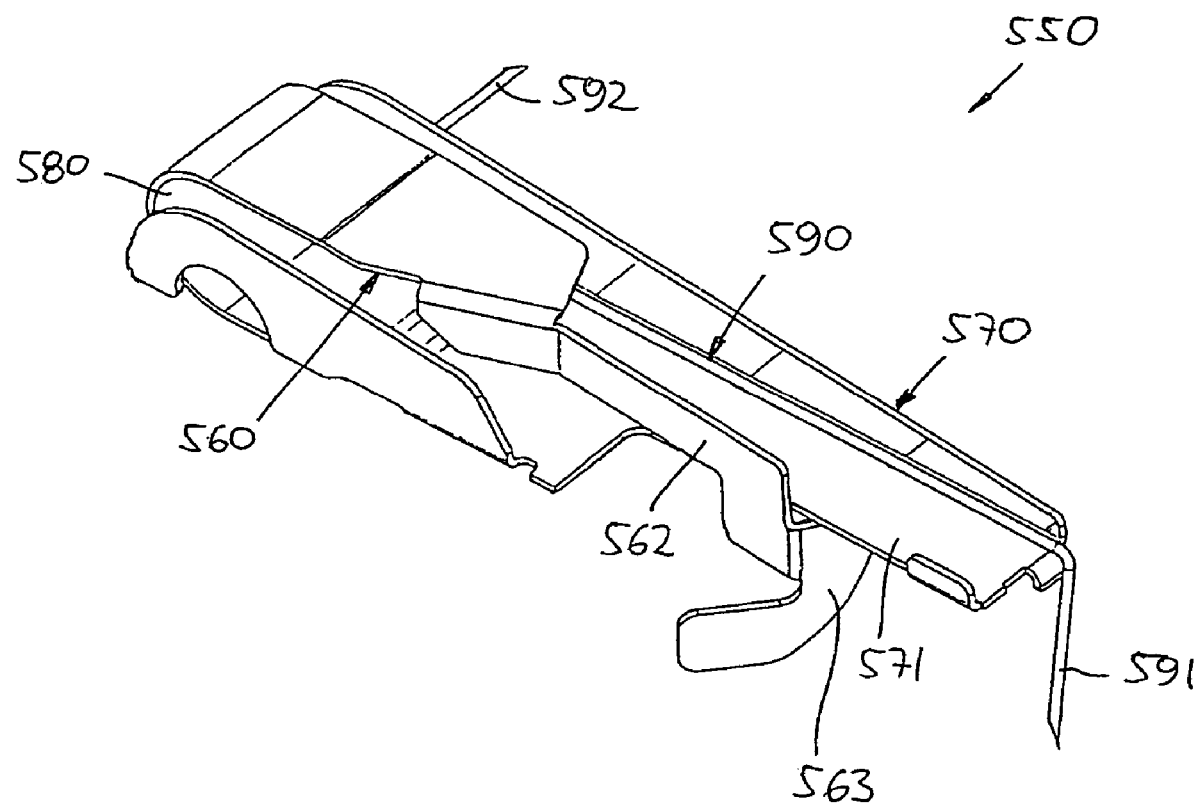
FIG. 7B shows a further transcutaneous device unit.

Thus FIG. 7B shows a further embodiment of a needle unit 550 adapted to be connected to a housing member to thereby allow the needle unit to pivot corresponding to a pivoting axis defined by a hinge. More specifically, the needle unit comprises a needle carrier formed from a bent sheet metal member, the carrier comprising an upper arm 560 and a lower arm 570 connected to each other by a hinge portion 580 allowing the arms to pivot corresponding to a pivoting axis defined by the hinge. The lower arm forms a tray 571 in which a hollow infusion needle 590 is mounted (e.g. by welding or adhesive), the needle having a distal pointed portion 591 adapted to penetrate the skin of the subject, the distal portion extending generally perpendicular to the mounting surface of a device in which it in a situation of use is mounted, and a proximal portion 592 arranged substantially corresponding to the pivoting axis. Thus, when a portion of the upper arm, e.g. the surface 561, is attached to a device housing, the lower arm can pivot between a first position in which the distal portion of the needle is retracted within a housing, and a second position in which the inlet portion projects relative to a mounting surface. The lower arm may be moved by external means, however, advantageously the needle unit provides the drive means for moving the lower arm between the two positions. This may be provided by the elastic properties of the sheet material per se corresponding to the hinge portion, or an additional spring may be provided between the two arms to thereby urge them apart. To lock the lower part in an energized, releasable first position, the upper arm is provided with a flexible release arm 562 comprising a catch 563 at the distal end thereof supporting and arresting the lower arm in its first position. When the distal end and the catch are moved away from the lower arm, the flexible properties of the hinge and/or the spring will bias the lower arm to its second position.

In the above described embodiments, the transcutaneous device has been in the form of a unitary needle device (e.g. an infusion needle as shown or a needle sensor (not shown)), however, the transcutaneous device may also be in the form of a combination of cannula or a sensor in combination with an insertion needle which is withdrawn after insertion thereof.

Figure 10A:
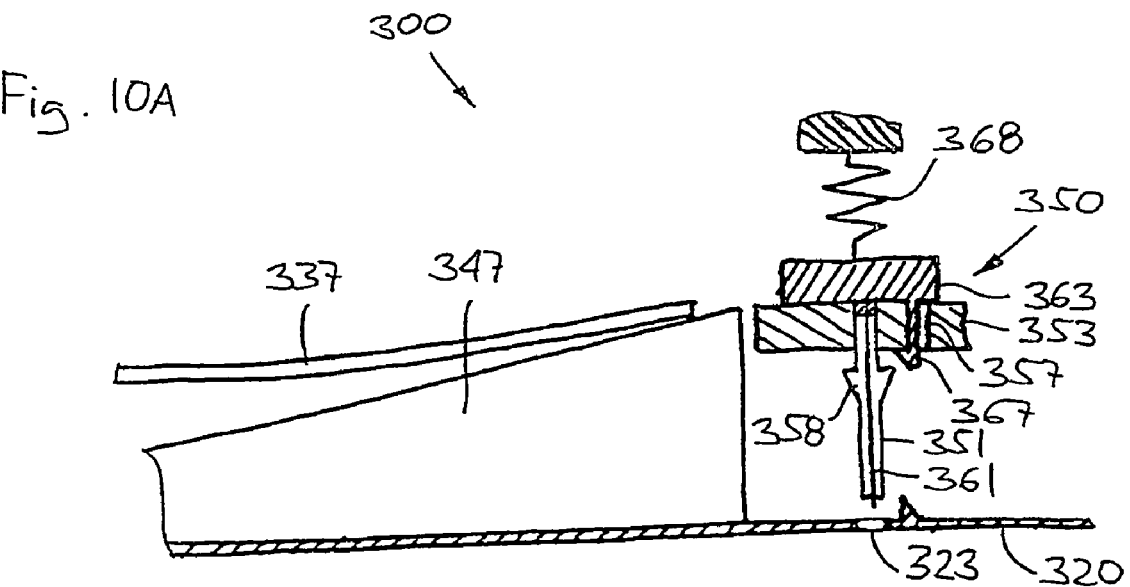
FIGS. 10A-10C show in a schematic representation a cannula and insertion needle combination implemented in a device.
Figure 10B:
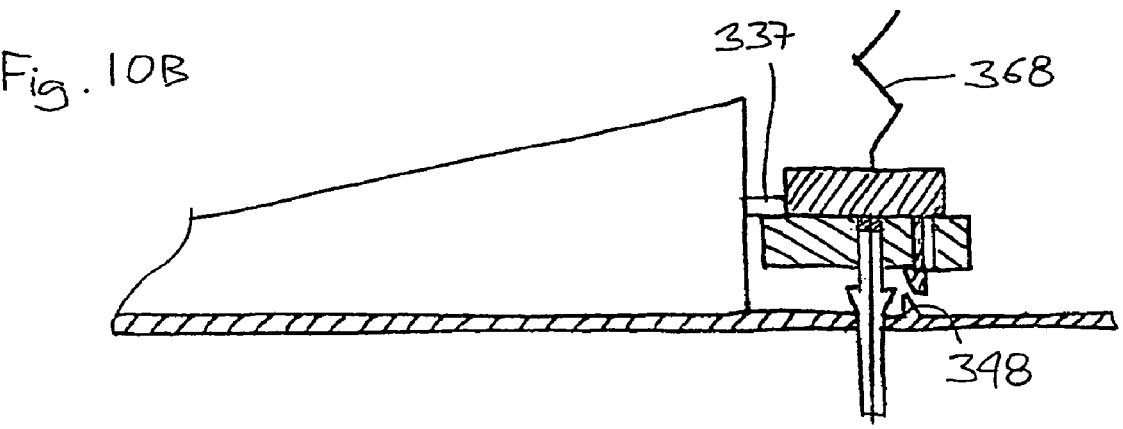
Figure 10C:
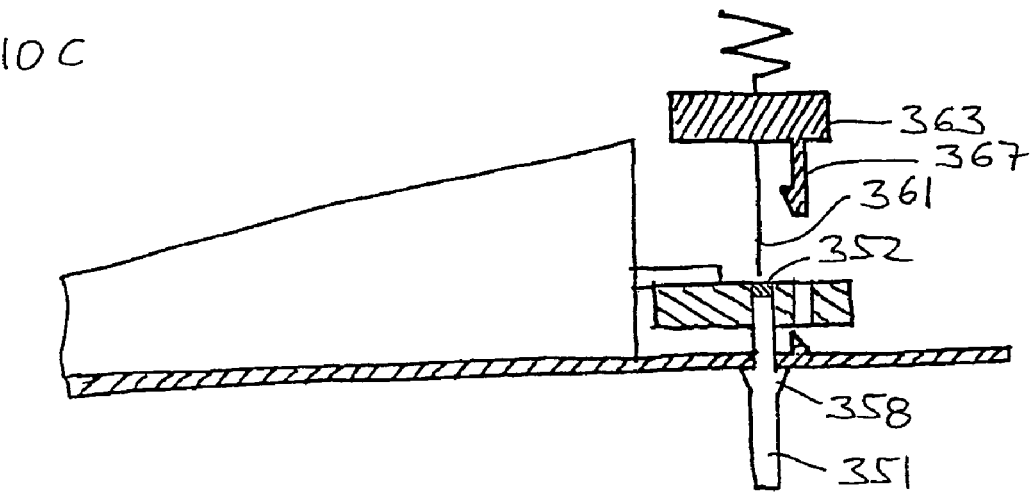

Thus, FIGS. 10A-10C show in a schematic representation how a cannula and insertion needle combination can be implemented in a device 300 (partly shown) of the type described with reference to FIGS. 4-6. More specifically, a transcutaneous device unit 350 of the type shown in FIG. 7 is provided, however, in contrast to the needle unit 150 the transcutaneous device unit comprises a combination of a relatively soft cannula 351 (which e.g. may be of the soft "Teflon®" type) carried by a lower arm portion 353 and a pointed insertion needle 361 (e.g. made from medical grade stainless steel) slidably arranged within the cannula and carried by an upper arm portion 363, both arm portions being attached to a hinge portion (not shown). The lower arm further comprises a seal member 367 through which the insertion needle is arranged. The cannula and the insertion needle may be straight or curved, e.g. arcuate corresponding to the pivoting axis. The two arms comprise mating coupling means 367, 357 locking the arms together in an initial position with distal end of the insertion needle extending from the distal opening of the cannula as shown in FIG. 10A. The cannula is provided with locking means adapted to engage the housing of the device when the cannula has been moved to an extended position. Between the housing of the device and the flexible arm a spring member 368 is arranged biasing the flexible arm upwards. Corresponding to the FIG. 4 embodiment, the device also comprises an inserter spring 337 and a ramp member 347, as well as a coupling release member 348.

In a situation of use the inserter spring is energized by being moved up the ramp by the user and then released to engage the lower arm to thereby pivot the transcutaneous device unit towards the extended position as shown in FIG. 10B. In its fully extended position the locking means of the cannula engages the housing of the device (here: an opening in the lower surface) and the coupling release member 348 engages the arm coupling means to thereby release the upper arm from the lower arm whereby the upper arm is moved towards its initial position by the spring member 368, thereby withdrawing the insertion needle from the cannula, see FIG. 10C. In the shown embodiment the cannula is irreversibly locked to the housing, however, advantageously releasable locking means is provided between the lower arm (or cannula) and the housing, this allowing the cannula to be withdrawn from its extended position before or after the used device is removed from the skin portion to which it has been attached.

In the above-described embodiments a medical device has been described comprising a reservoir, however, for better illustrating the principles of the present invention, the means for expelling a drug from the reservoir has been omitted in the figures. Such expelling means, which as the reservoir does not form part of the present invention in its basic form, may be of any type which would be suitable for arrangement within a skin-mountable drug delivery device. Further, as the needle of the present invention also may be in the form of a needle sensor, the interior of the medical device may comprise sensor means adapted to cooperate with the needle sensor.

Figure 8A:
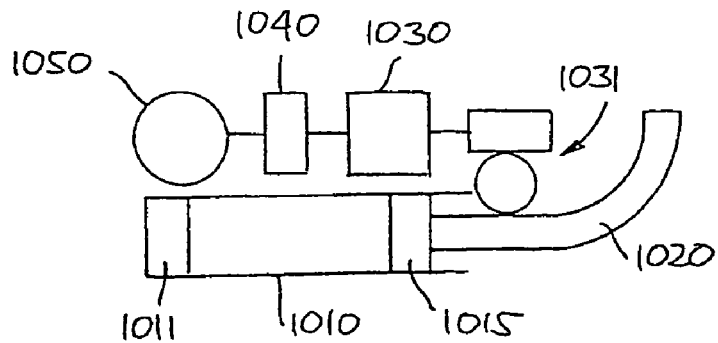
FIGS. 8A-8D shows different expelling means suitable for use with the invention.

In FIGS. 8A-8D examples of expelling means suitable for use with the present invention are shown schematically, however, these are merely examples. More specifically, FIG. 8A shows a pump arrangement comprising a drug-containing cartridge 1010 having a distal closure member 1011 allowing a needle to be connected, and a piston 1015 slidingly arranged there within, a flexible toothed piston rod 1020 (for example as disclosed in U.S. Pat. No. 6,302,869), an electric motor 1030 which via a worm-gear arrangement 1031 drives the piston rod to expel drug from the cartridge, the motor being controlled by control means 1040 and the energy for the control means and the motor being provided by a battery 1050. The pump may be activated when the needle is inserted (by means not shown) or by separate user-actuatable means (not shown) after the inserter has been detached form the delivery device.

Figure 8B:
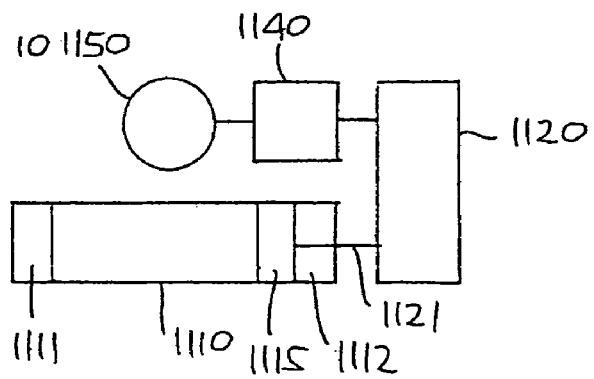

FIG. 8B shows a pump arrangement comprising a drug-containing cartridge 1110 having distal and proximal closure members 1111, 1112, and a piston 1115 slidingly arranged there within, gas generating means 1120 in fluid communication with the interior of the cartridge via conduit 1121 for driving the piston to expel drug from the cartridge, the gas generating means being controlled by control means 1140 and the energy for the control means and the gas generation being provided by a battery 1150. The pump may be activated as indicated above. A detailed disclosure of such gas generating means for a drug delivery device can be found in e.g. U.S. Pat. No. 5,858,001.

Figure 8C:
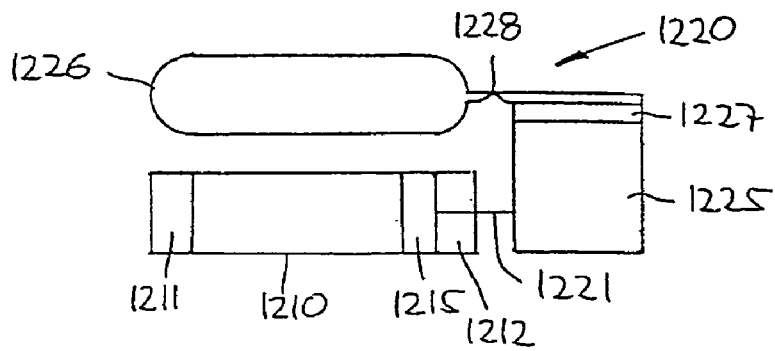

FIG. 8C shows a pump arrangement comprising a drug-containing cartridge 1210 having distal and proximal closure members 1211, 1212, and a piston slidingly 1215 arranged there within, an osmotic engine 1220 in fluid communication with the interior of the cartridge via conduit 1221 for driving the piston to expel drug from the cartridge. The osmotic engine comprises a first rigid reservoir 1225 containing a salt-solution and a second collapsible reservoir 1226 containing water, the two reservoirs being separated by a semipermeable membrane 1227. When supplied to the user, the fluid connection 1228 between the second reservoir and the membrane is closed by a user-severable membrane (e.g. a weak weld) which, when severed, will allow the osmotic process to start as water is drawn from the second reservoir through the membrane and into the first reservoir. The pump may be activated as indicated above. A detailed disclosure of the osmotic drive principle can be found in e.g. U.S. Pat. No. 5,169,390.

Figure 8D:
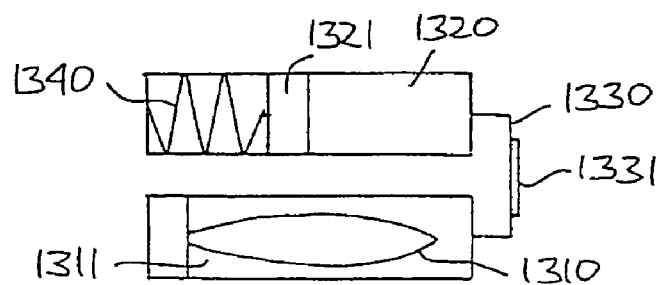

FIG. 8D shows a pump arrangement comprising a drug-containing flexible reservoir 1310 arranged within a rigid fluid-filled secondary reservoir 1311 in fluid communication with a primary reservoir 1320 through a conduit 1330 comprising a flow restrictor 1331. The primary reservoir is in the form of a cartridge with a moveable piston 1321 and contains a viscous drive fluid. A spring is arranged to act on the piston to drive fluid from the first to the second reservoir thereby expelling drug from the flexible reservoir when the latter is connected to an infusion needle (not shown). The flow rate will be determined by the pressure generated by the spring in the drive fluid, the viscosity of the drive fluid and the flow resistance in the flow restrictor (i.e. bleeding hole principle). The pump may be activated by straining the spring or by releasing a pre-stressed spring, either when the needle is inserted (by means not shown) or by separate user-actuatable means (not shown) after the inserter has been detached form the delivery device. An example of this principle used for drug infusion is known from DE 25 52 446. In an alternative configuration, the drug reservoir may be pressurized directly to expel the drug via a flow restrictor, e.g. as disclosed in U.S. Pat. No. 6,074,369.

In the above-described embodiments the needle unit has been adapted primarily for actuation by actuatable driving means, however, with reference to FIGS. 9A-9F a drug infusion device is shown which is adapted for manual actuation by moving an actuation member in parallel with the mounting surface.

More specifically, a drug infusion device 901 comprises a base plate 910, a first cover member 920 and a second cover member 930, the three elements in combination forming a housing in which a pump assembly 940 and a flexible drug reservoir 950 are arranged.

The base plate comprises a lower generally planar surface 918 adapted to be mounted in engagement with a skin-surface of a user, and an upper surface 919 provided with connecting means allowing the first and second cover members as well as a pump assembly 940 to be mounted on the base plate. More specifically, the base plate comprises three upstanding hook-members 911 adapted to engage corresponding hook structures 921 on the first cover member to thereby lock the two members to each other in a snap-action manner, as well as a pair of parallelly arranged opposed members 912 having outwardly open grooves adapted to engage corresponding flange structures 931 on the second cover member allowing the two members to be mounted in sliding engagement with each other. In order to control movement between the two members, the grooves and the flanges may be provided with corresponding ratchet or locking means 916, 932. To help align the second cover member as it is moved towards the first cover member, the base plate comprises a ridge member 913 adapted to engage a corresponding groove structure 933 on the second cover member. The base plate member further comprises an aperture 914, a part-cylindrical "female" hinge member 915 adapted to engage the pump assembly, as well as an opening 917 associated with the hinge member.

The pump assembly 940 comprises a membrane pump as well as control means, actuating means (e.g. heating means), contact means and an energy source for driving the pump. The pump assembly is configured with a (part) cylindrical hinge body 941 from which protrudes a pump body 942 wherein the pump and driving means are arranged. On the lower surface of the hinge body an engagement member 947 is arranged. The pump inlet is in fluid communication with an inlet needle 943 protruding axially from an end of the hinge body and the pump outlet is in fluid communication with an infusion needle 944 protruding from a lower surface 948 of the pump body, both needles having a pointed free end. The hinge body is adapted to be pivotally received in the hinge member 915 with the engagement member 947 arranged in the opening 917 to prevent axial displacement of the pump assembly, and with the infusion needle in alignment with the aperture 914.

The flexible reservoir 950 is in the form of a pouch- or bag-like member formed from a pliable material and provided with a needle penetratable connecting means, e.g. a self-sealing septum (not shown). The reservoir is easily collapsible allowing the drug contained therein to be sucked out by the pump without the need for additional venting means. The reservoir is mounted and hold in place under the second cover member by appropriate means. In the shown embodiment the reservoir is prefilled with a drug such as insulin, however, the reservoir may also be adapted to be filled by the user prior to user.

The above-described components are assembled in two subassemblies (see FIGS. 9C and 9D), a main assembly 960 and a reservoir assembly 970, this allowing the assemblies to be sterilized independently if necessary. More specifically, the main assembly comprises the base plate member with the first housing member mounted on top thereof providing a cavity in which the pump assembly 940 is pivotally arranged in the hinge member 915, and the reservoir assembly comprises the second housing member with the reservoir mounted corresponding to a lower surface thereof. The hinge may be configured to provide an upwardly biasing force preventing the pump assembly from pivoting downwardly.

The second housing member is provided with an end portion having a grooved area 934 and an oppositely arranged shroud portion 935 adapted to slide under the first cover member, as well as a lower ramp member 936 associated with the lower surface of the second housing member, the function of which will be explained in greater detail below.

Figure 9E:
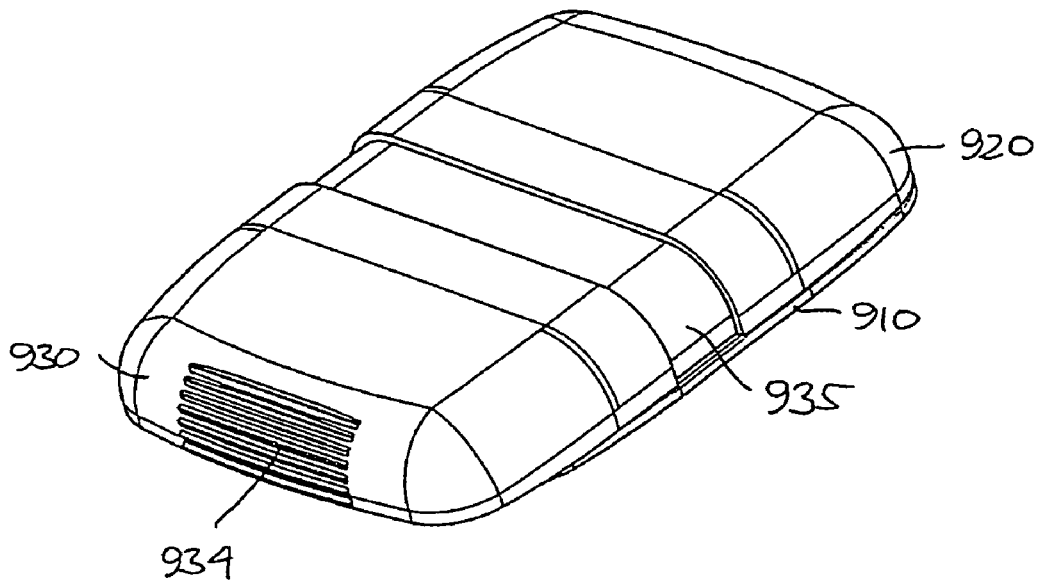
FIG. 9E shows the infusion device in an assembled initial state.
Figure 9F:
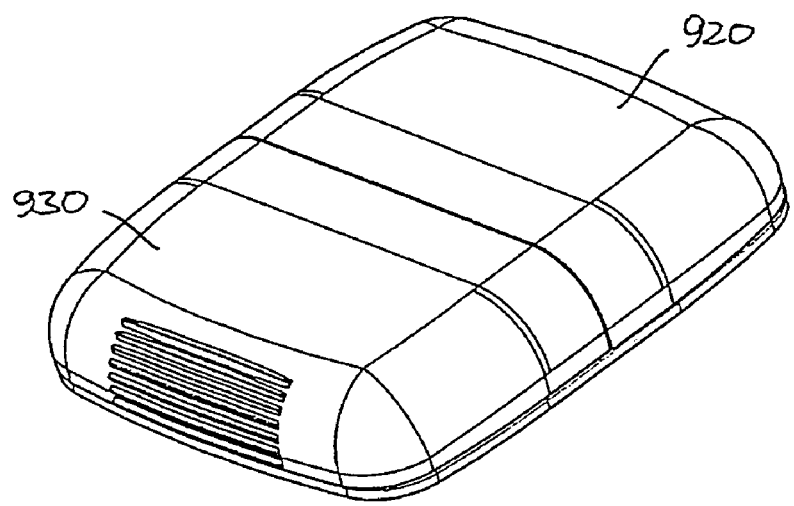
FIG. 9F shows the infusion device in an assembled actuated state.

The drug infusion device 901 is supplied to the user with the two subassemblies assembled corresponding to an initial state as shown in FIG. 9E. More specifically, the reservoir assembly is mounted in sliding engagement with the base plate member by means of the connecting members 912, 931, a cavity inclosing the reservoir thereby being formed between the second cover member and the base plate member, the reservoir connecting means being arranged in axial alignment with the inlet needle. In the initial state the reservoir assembly is not fully moved towards the first cover member, however, the shroud is partially inserted under the first cover member, this providing a closed cavity. The locking or ratchet means 916, 932 arranged between the second cover member and the base plate member may be configured to prevent that the reservoir assembly can be removed by the user.

To activate the infusion device, the reservoir assembly is moved towards the pump assembly (see FIG. 9F) whereby a number of actions takes place. More specifically, the inlet needle 943 will penetrate the reservoir connecting means providing fluid communication between the reservoir and the pump, and the ramp 936 on the second cover member will engage the pump assembly to thereby pivot it downwardly whereby the infusion needle 944 will be moved through the aperture 914. At the same time contact means arranged on the pump assembly (e.g. on the lower surface of the pump body) will be activated, thereby activating the pump control means and eventually the pump, however, the activated control means may be adapted to "wait" for a command signal from an external signal (e.g. supplied from a remote control device) before the pump is actuated. In an alternative embodiment (not shown) the reservoir assembly and the pump assembly may be adapted to move linearly, e.g. in a co-linear fashion when arranged in a "stack". In further alternative embodiments (not shown) the reservoir may be connected to the pump, the pump being started, and the needle introduced partly or fully independently of each other, e.g. by two or three user actuated actions.

The drug infusion device 901 may be used in the following way. After the liner has been removed the device is place on a suitable skin portion of the user, e.g. in the abdominal region after which the reservoir assembly serving as a button (indicated by the grooved area 931) is pushed towards the main portion until it locks in place, this, as described above, resulting in activation of the pump and introduction of the needle subcutaneously through the skin of the user. Depending on the programming of the control means, the pump may start to operate immediately or it may wait for user activated commands before pump action is initiated, e.g. commands received from a remote commander or from input means arranged on the device. Before infusion in accordance with a given (basal) infusion rate begins, the pump will advantageously perform a priming action as described above. As the volume of air initially trapped in the infusion pump and the associated conduits (including the two needles) normally is very small, it will in most cases be acceptable to expel this volume of air into the user, however, if this is not desirable, actuation of the infusion device (i.e. pushing the two assemblies together) will have to be performed before the device is mounted on the skin.

When the device is to be removed, it may be pulled of the skin in its active state with the needle protruding from the lower surface, or the device may be reversed to its initial state before it is removed. For example, if locking means are arranged between the shroud and the first cover member, the locking means may be released by pushing down the upper surface of the first cover member.

In the above described embodiments, the needle has been in the form of a unitary needle device (e.g. an infusion needle as shown or a needle sensor (not shown)), however, a needle device (e.g. a soft cannula or a soft needle sensor) may also be introduced subcutaneously in combination with an insertion needle which is withdrawn after insertion thereof.

Thus, in a further embodiment the needle unit comprises an insertion needle having a distal pointed end, the insertion needle being removeably arranged co-axially with and supporting the distal needle portion (e.g. of a needle sensor), the insertion needle and the needle being arranged to be simultaneously pivoted from their respective first position to their respective second position when the needle unit is actuated. The insertion needle may have any desirable configuration such as solid or grooved.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

CITED DOCUMENTS THAT ARE
INCORPORATED BY REFERENCE

U.S. Pat. No. 4,340,048
U.S. Pat. No. 4,552,561
U.S. Pat. No. 5,858,001
U.S. Pat. No. 6,280,148
U.S. Pat. No. 5,957,895
U.S. Pat. No. 5,527,288
U.S. Pat. No. 2,605,765
U.S. Pat. No. 4,340,048
EP 1 177 802
U.S. Pat. No. 5,814,020
U.S. Pat. No. 5,931,814
WO 02/15965

The invention claimed is:
1. A medical device, comprising:
a housing having a mounting surface adapted for application to the skin of a subject,
a transcutaneous device unit comprising a transcutaneous device carrier that does not contain a pump or pump drive means, the unit being connected to the housing thereby providing a pivot hinge allowing the transcutaneous device unit or a portion thereof to pivot corresponding to a pivoting axis defined by the pivot hinge, the pivoting axis being arranged substantially in parallel with the mounting surface,
wherein the transcutaneous device unit comprises a transcutaneous device carried by or formed integrally with the transcutaneous device carrier, the transcutaneous device comprising a distal pointed portion adapted to penetrate the skin of the subject, the distal portion extending generally perpendicular to the mounting surface, and a proximal portion arranged substantially along the pivoting axis,
wherein the transcutaneous device unit is arranged to provide corresponding to the pivoting axis a pivoting movement between a first position in which the distal pointed portion of the transcutaneous device is retracted within the housing, and a second position in which the distal pointed portion of the transcutaneous device projects relative to the mounting surface.

2. A medical device as defined in claim 1, further comprising:
- a reservoir adapted to contain a liquid drug and comprising in a situation of use an outlet in fluid communication with the transcutaneous device, and
- expelling means for expelling a drug out of the reservoir and through the skin of the subject via the transcutaneous device.

3. A medical device as defined in claim 2, wherein the reservoir comprises outlet means adapted to cooperate with the proximal portion of the transcutaneous device, the outlet means being arranged substantially corresponding to the pivoting axis, thereby allowing the transcutaneous device unit to pivot substantially without non-rotational displacement of the proximal portion of the transcutaneous device relative to the outlet means.

4. A medical device as defined in claim 3, wherein the reservoir and the proximal portion are moveable relative to each other substantially in parallel with the pivoting axis, between a disconnected position in which there is no fluid communication between the reservoir and the proximal portion of the transcutaneous device, and a connected position in which fluid communication between the reservoir and the proximal portion of the transcutaneous device is established.

5. A medical device as defined in claim 4, wherein the proximal portion of the transcutaneous device comprises a pointed end, and the outlet means of reservoir comprises a needle-penetratable septum.

6. A medical device as defined in claim 1, further comprising actuatable driving means disposed within the housing and adapted to pivot the transcutaneous device unit from the first position to the second position.

7. A medical device as defined in claim 6, further comprising actuation means moveable, relative to the housing, from a first position to a second position thereby actuating the driving means.

8. A medical device as defined in claim 7, wherein a reservoir is connected to the actuation means, whereby movement of the actuation means between the first and the second position causes the reservoir to be arranged in fluid communication with the transcutaneous device infusion needle.

9. A medical device as defined in claim 5, further comprising actuation means moveable, relative to the housing, from a first position to a second position thereby actuating the driving means, wherein the reservoir is connected to the actuation means such that movement of the actuation means between the first and the second position causes the reservoir to be arranged in fluid communication with the transcutaneous device, the proximal portion of the transcutaneous device being introduced through the needle-penetratable septum either before or after the transcutaneous device unit is pivoted from the first position to the second position.

10. A medical device as defined in claim 1, wherein the transcutaneous device is a unitary hollow infusion needle forming the distal and proximal portions.

11. A medical device as defined in claim 1, wherein the distal portion is formed by a cannula in combination with a pointed insertion needle accommodated at least partially within the cannula, the cannula having a distal opening, wherein the insertion needle is arranged to be moveable away from the distal opening when the cannula and the insertion needle have been moved to their second position.

* * * * *

UNITED STATES PATENT AND TRADEMARK OFFICE
CERTIFICATE OF CORRECTION

| | | |
|---|---|---|
| PATENT NO. | : 7,628,770 B2 | Page 1 of 1 |
| APPLICATION NO. | : 11/266821 | |
| DATED | : December 8, 2009 | |
| INVENTOR(S) | : Ethelfeld | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 403 days.

Signed and Sealed this
Eleventh Day of January, 2011

David J. Kappos
*Director of the United States Patent and Trademark Office*